United States Patent [19]

Puno et al.

[11] Patent Number: 4,805,602
[45] Date of Patent: Feb. 21, 1989

[54] TRANSPEDICULAR SCREW AND ROD SYSTEM

[75] Inventors: Rolando M. Puno, Louisville, Ky.; Kevin A. Kelly, Columbus, Ohio

[73] Assignee: Danninger Medical Technology, Columbus, Ohio

[21] Appl. No.: 926,386

[22] Filed: Nov. 3, 1986

[51] Int. Cl.⁴ ............................ A61F 5/00; A61B 17/18
[52] U.S. Cl. .................................. 128/69; 128/92 ZK; 128/92 ZW; 128/92 YS; 128/92 YM; 403/342; 403/399; 439/804; 24/135 N; 24/486
[58] Field of Search ............ 128/92 YM, 92 YF, 92 Z, 128/69; 403/342; 24/486, 135 N, 130, 135 R; 623/16, 17; 82/37; 248/251, 316.6; 211/123, 7; 411/400, 401

[56] References Cited

U.S. PATENT DOCUMENTS

| | | | |
|---|---|---|---|
| 296,310 | 4/1884 | Bowman | 82/37 |
| 476,227 | 5/1892 | Dunning | 411/400 X |
| 492,593 | 2/1893 | Taylor | 248/74.4 |
| 905,648 | 12/1908 | Chamberlain | 82/37 |
| 1,201,864 | 10/1916 | Overmeyer | 128/92 ZW |
| 2,136,091 | 11/1938 | Tiefebacher | 82/37 |
| 2,346,346 | 4/1944 | Anderson | 128/92 Z |
| 2,833,183 | 5/1958 | Zierden | 82/37 |
| 2,914,284 | 7/1958 | Tisdall | 248/251 |
| 3,997,138 | 12/1976 | Crock et al. | 128/92 R X |
| 4,041,939 | 8/1977 | Hall | 128/92 YF X |
| 4,273,116 | 6/1981 | Chiquet | 128/92 ZW X |
| 4,289,124 | 9/1981 | Zickel | 128/92 YF |
| 4,369,769 | 1/1893 | Edwards | 128/92 YP X |
| 4,569,338 | 2/1986 | Edwards | 128/92 YF X |
| 4,611,580 | 9/1986 | Wu | 128/69 |
| 4,611,582 | 9/1986 | Duff | 128/69 |
| 4,648,388 | 3/1987 | Steffee | 128/92 YF X |

FOREIGN PATENT DOCUMENTS

| | | | |
|---|---|---|---|
| 58639 | 10/1953 | France | 339/265 R |
| 206262 | 7/1939 | Switzerland | 24/135 N |
| 522747 | 6/1940 | United Kingdom | 24/486 |

Primary Examiner—Richard J. Apley
Assistant Examiner—David J. Bender
Attorney, Agent, or Firm—Pearne, Gordon, McCoy & Granger

[57] ABSTRACT

An apparatus is provided for the internal fixation of the spine. The apparatus comprises two sets of implants each consisting of a rod and a plurality of vertebral anchors. A set of implants is positioned on the spine on either side of the spinous process spanning the portion of spine to be immobilized. The rod is secured to the vertebral laminae by the vertebral anchors. The anchor includes a transpedicular screw member which is secured to a vertebrae. A rod support includes a cup which captures the screw and optionally permits micromotion between the rod support and screw. The rod support also includes a rod-receiving channel which captures the rod. A clamp is provided to secure the rod in the channel.

7 Claims, 4 Drawing Sheets

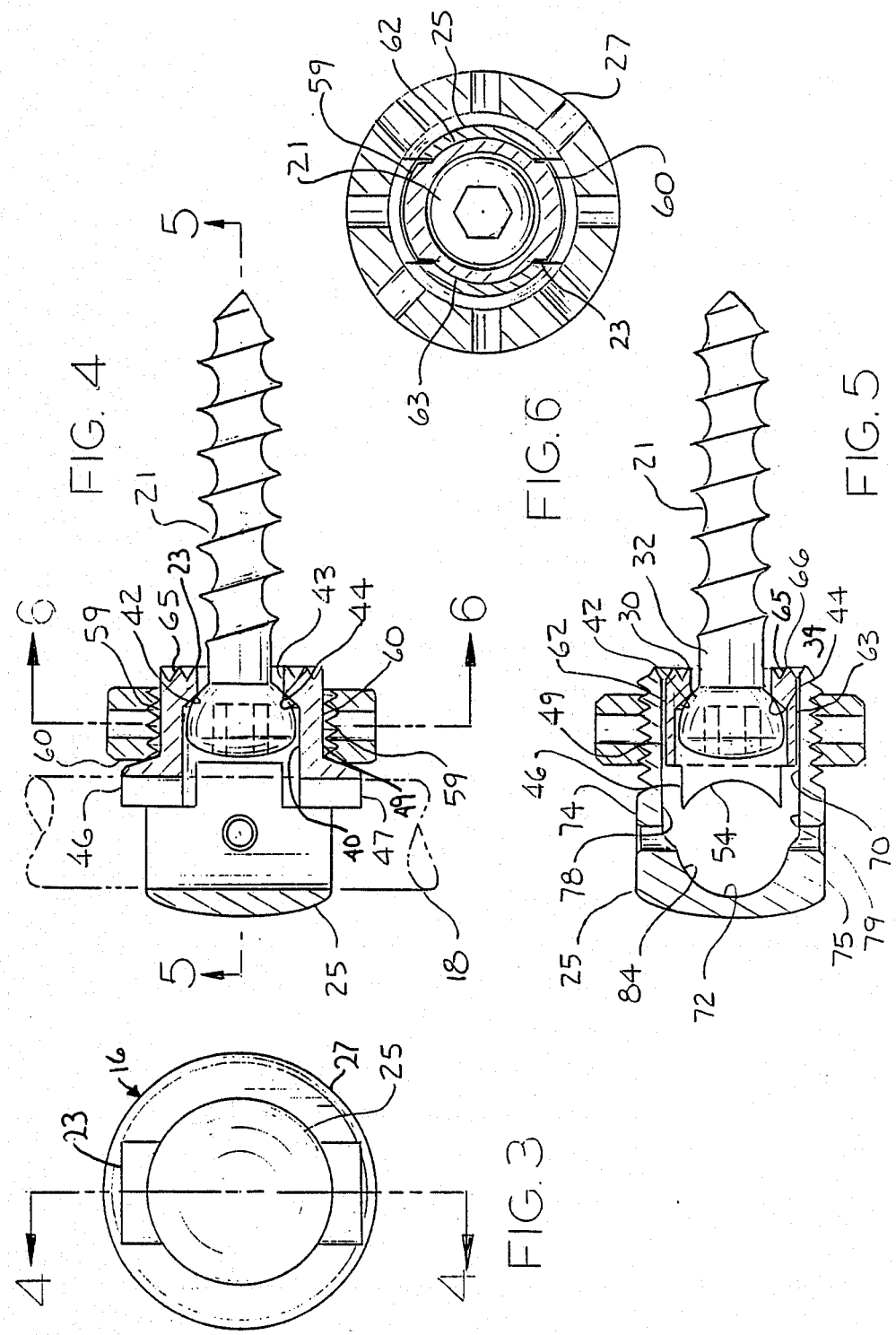

TRANSPEDICULAR SCREW AND ROD SYSTEM

BACKGROUND OF THE INVENTION

The invention relates generally to an apparatus for immobilization of the spine, and more particularly, to an apparatus for posterior internal fixation of the spine.

Various methods of spinal immobilization have been known and used during this century in the treatment of spinal instability and displacement. The preferred treatment for spinal stabilization is immobilization of the joint by surgical fusion, or arthrodesis. This method has been known since its development in 1911 by Hibbs and Albee. However, in many cases, and in particular, in cases involving fusion across the lumbosacral articulation and when there are many levels involved, pseudoarthrosis is a problem. It was discovered that immediate immobilization was necessary in order to allow a bony union to form. Early in the century, post operative external immobilization such as the use of splints and casts was the favored methods of treatment, however, as surgical techniques have become more sophisticated, various methods of internal and external fixation have been developed.

Internal fixation refers to methods of stabilization which are wholly internal to the patient and include commonly known devices such as bone plates and pins. External fixation in contrast involves at least some portion of the stabilization device which is external to the patient's body. Internal fixation is now the favored method of immobilization since the patient is allowed greater freedom with the elimination of the external portion of the device and the possibility of infections, such as pin tract infection, is reduced.

Some of the indications treated by internal fixation of the spine include vertebral displacement and management such as kyphosis, spondylolishtesis and rotation; segmental instability, such as disc degeneration and fracture caused by disease and trauma and congenital defects; and tumor diseases.

A common problem with spinal fixation is the question of how to secure the fixation device to the spine without damaging the spinal cord. The pedicles are a favored area of attachment since they offer an area that is strong enough to hold the fixation device even when the patient suffers from osteoporosis. Since the middle 1950's, methods of fixation have utilized the pedicles. In early methods, screws extended through the facets into the pedicles. More recently, posterior methods of fixation have been developed which utilize wires that extend through the spinal canal and hold a rod against the lamina (such as the Luque system) or that utilize pedicular screws which extend into the pedicle and secure a plate which extends across several vertebral segments (such as the Steffe plate).

The present invention presents a new system sharing advantages of both the wired implants and the plate. Specifically, the screw and rod system of the present invention provides a rigidity which is intermediate the wired implant and the plate systems. While the screw and rod system of the present invention retains the stability provided by the plate and screw system, the present invention may be contoured to any plane.

In particular, the present invention is viewed as having an application in the stabilization of the thoracolumbar, lumbar, and sacral spine. There are problems of fixation unique to this area of the spine such as the fact that the lumbar spine is normally lordotic and this lordosis must be preserved. In addition, indicated spinal decompression often requires a destabilization of the spine posteriorly. This may result in instability unless fusion is used, and fusion will often fail to become solid unless effective internal fixation is used. Finally, the points of sacral fixation are the weakest point of fixation. These problems are addressed by the present invention.

Prior Art

Prior art devices for posterior spinal fixation are discussed above as including the Steffe plate and the Luque System. A complete discussion of various internal fixation devices are included in L. Wiltse, "Internal Fixation of the Lumbar Spine", *Clinical Orthopaedics and Related Research,* Feb. 1986, No. 203, p.p. 2–219. Known implant configurations include facet screws, double distraction systems, compression distraction systems, springs, spinous process plates, wired implants and transpedicular screw and plate systems.

Common distraction and compression systems utilize a threaded rod and hooks which engage selected transverse processes of the vertebrae. Examples of such systems include the Harrington distraction system sold by Zimmer USA, Inc., the Keene system shown in U.S. Pat. No. 4,269,178 and the Lewis-Greenlaw System illustrated in U.S. Pat. No. 4,085,744. U.S. Pat. No. 3,648,691 to Lumb et al. shows the use of spinous process plates.

Wired implants are favored by some orthopedic surgeons because of the flexibility of the system. Dr. Eduardo Luque has developed a wired implant system where two L-shaped rods are secured along their long sides to the vertebral laminae by means of wires which pass through the vertebral foramina. The short legs of the rods extend across the vertebrae between the spinous process. A similar wired implant is shown in U.S. Pat. No. 4,604,995 to Stephens et al.

Transpedicular screw and plate systems rely on a screw threaded into a reemed canal generally positioned perpendicular to the longitudinal axis of the spine and horizontal or parallel to the anterior/posterior plane of the vertebral body. Methyl methacrylate is sometimes used to secure the screw in the canal, particularly if osleoporesis is a problem. The screws engage a plate which has been bent to conform to the normal curvature of the spine or to the points of desired reduction. One screw and plate system which has been used with significant success is the Steffee system. In this system, the screws are inserted first, the spine plates are then inserted over the pedicle screws and then posterior tapered nuts are screwed on. The screws are tightened bilaterally until the plate is locked between two nuts.

While the wired implants have the advantages of facilitating vertebral alignment, permitting variation of the device to allow for variations in individual spines, and decreasing rigidity, this method of fixation includes the increased risk of damage to the neural structures. This risk can be countered by the use of transpedicular screws and plates. The pedicle presents an area for fixation of sufficient size and depth, that under careful conditions, the risk of damage to the nerve chord is reduced. On the other hand, the use of plates with the screws is more rigid than the wired implants and the tension and compression of the plate on the screw can cause dislocation or even shearing of the screw. In addition, the current plate designs are bulky and leave little surface for bone grafting and they cannot be contoured to any lateral curvature of the spine.

SUMMARY OF THE INVENTION

The present invention utilizes a rod and vertebral anchors which holds the rod in position against the vertebral lamina. Each anchor is secured to the vertebrae by a transpedicular screw member.

The screw and rod system of the present invention combines favorable attributes discussed above of wire implants and of screw plate systems. In particular, the present invention has an object of providing a fixation system which adequately immobilizes the lumbosacral area, allows relatively simple and risk-free insertion and provides adequate area for bone grafting.

Thus, the present invention combines advantages of the known devices as it provides suitable immobilization, in particular of the lumbosacral region; it allows for adaptation to individual patient characteristics such as degree of sagittal and/or cornonal plane curvature; it allows for safe and relatively risk-free insertion; and it permits sufficient area for bone grafting.

In order to achieve these advantages, the present design utilizes two implant sets on either side of the spinous process. Each implant set includes a 0.25 inch stainless steel (316L) rod which spans the vertebrae to be immobilized. Generally, an implant set is used on each side of the spinous process on the posterior side of the laminae and the transverse process. The rod is held in position by a stainless steel vertebral anchor which captures the rods. The anchor is secured to the vertebrae by a stainless steel transpedicular screw. The screw is preferably separate from the anchor but could also form an integral part of the screw.

In the preferred embodiment, the anchor comprises three members; a rod support having a cup which contains the screw and a rod-receiving channel transverse to the screw; a clamp having a central arch which mates with the rod support to capture the rod; and an internally threaded collar or nut which engages external threads on the clamp to tighten the clamp into position on the rod support. The collar includes holes so that a crimping tool can be inserted to partially strip the clamp threads to prevent loosening but still allow removal of the nut with the use of a wrench.

BRIEF DESCRIPTION OF THE DRAWINGS

FIG. 3 is a top plan view of the vertebral anchor of the first embodiment invention;

FIG. 4 is a cross-section of the vertebral anchor and screw taken along line 4—4 with the rod shown in phantom;

FIG. 5 is a cross-section of the vertebral anchor and screw shown in FIG. 4 taken along line 5—5;

FIG. 6 is a cross-section of the vertebral anchor and screw shown in FIG. 4 taken along line 6—6;

DETAILED DESCRIPTION OF THE DRAWINGS

Figure 1:
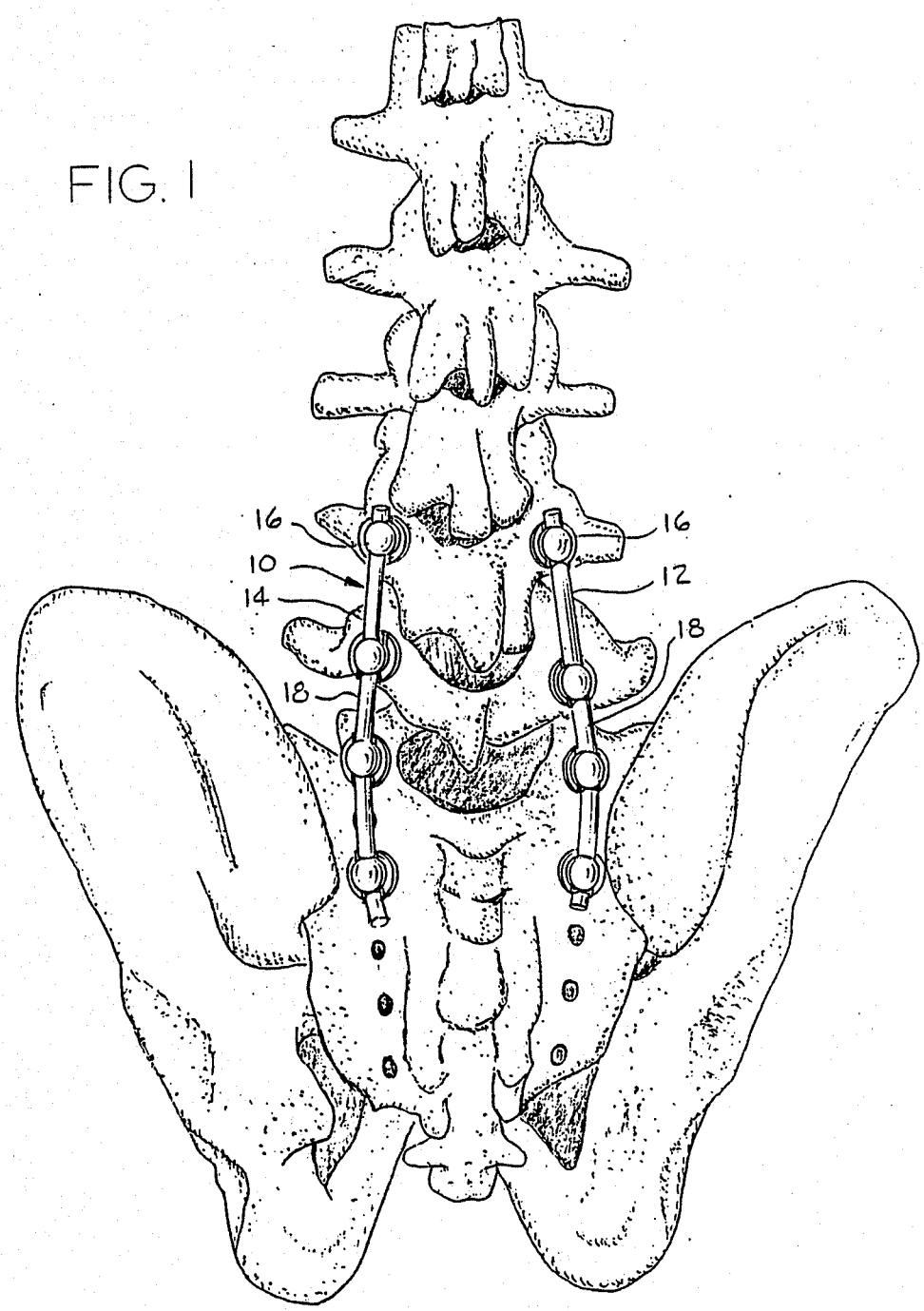
FIG. 1 is a posterior perspective view of a spine with the invention in place.
Figure 2:
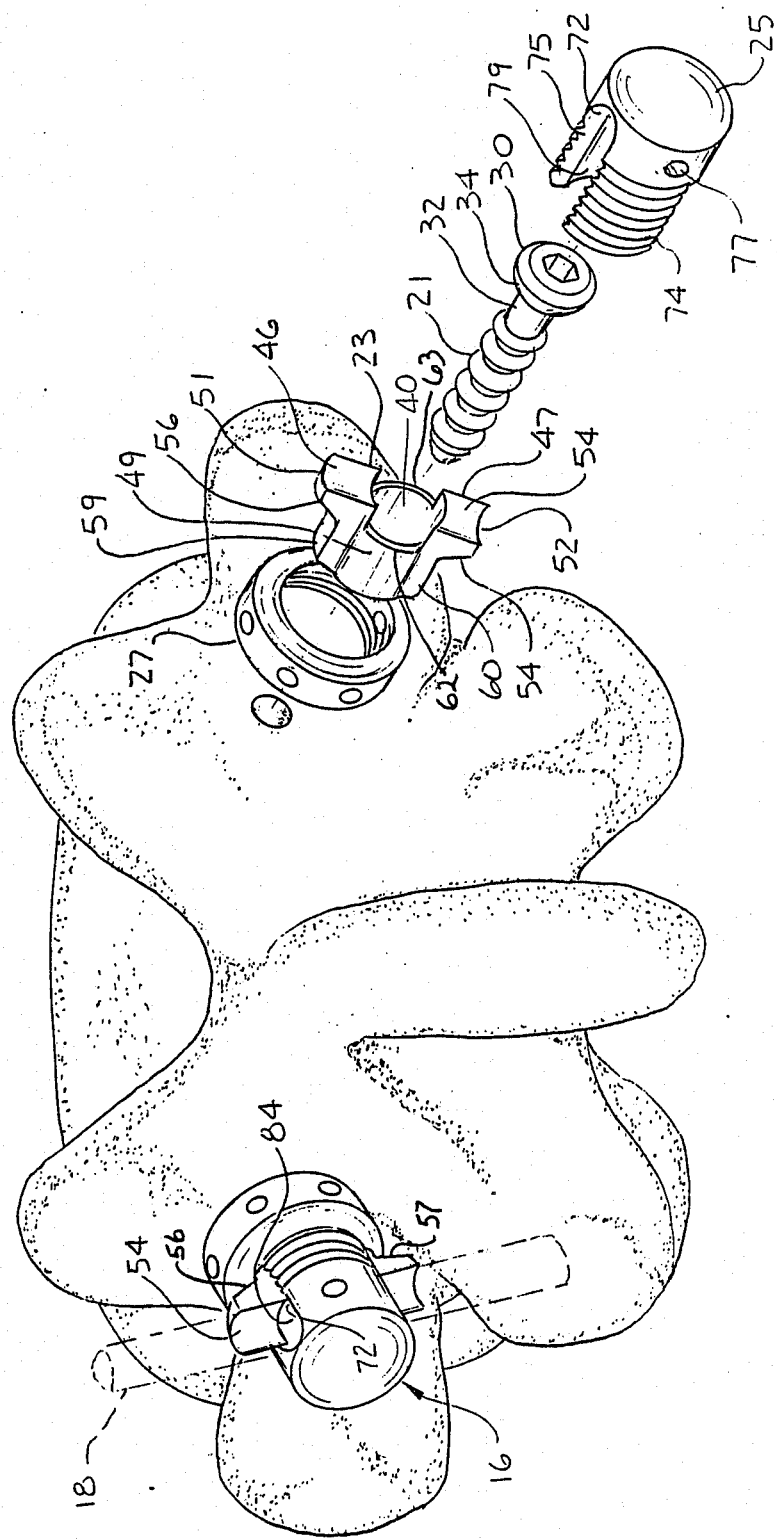
FIG. 2 is a posterior perspective view of a vertebral body with a vertebral anchor in position and an exploded view of the first embodiment of the invention.

The screw and rod system 10 of the present invention includes two implant sets 12, 14 on either side of the spinous process. Each set is comprised of a plurality of vertebral anchors 16 and a rod 18 which is of sufficient length to span the length of spine to be immobilized.

Each anchor 16 is positioned on the dorsal side of the transverse process and in general, a separate anchor 16 is used for each vertebrae comprising the length of spine to be stabilized. The rod 18 is held by the anchors 16 inside the curve of the transverse process posterior to the vertebral laminae.

The rod 18 is generally made of quarter inch stainless-steel rod (316 L), but could be made of any material which has suitable biocompatibility and material strength characteristics. The rod should be able to withstand lateral bending forces and torsion since the system may be used to correct spinal displacement and curvature. On the other hand, it is important that the rod 18 can be bent to a certain extent so that the rod can be bent to the proper curvature for the individual application.

In the preferred embodiment, the vertebral anchor 16 comprises a transpedicular screw 21, a rod support 23, a clamp 25 and a collar 27. The anchor 16 can be made of any suitably strong biocompatible material such as stainless steel. The screw 21 which is shown is a standard 6.5 millimeter stainless steel cancellous screw. The anchor 16 was designed for use with this screw since the screw is readily available, it has a proven record in fracture fixation; and the size can be accommodated by the average adult pedicles of the lower thoracic, lumbar and the upper two sacral segments vertebrae.

The screw 21 includes a head 30 which accommodates a hex driver. The screw 21 includes a smooth shank 32 of 2-4 millimeters length which joins the rounded rear shoulder 34 of the head 30. After insertion, the screw 21 extends from the curve formed on the dorsal side of the transverse process into the bony area above the neural arch.

The rod support 23 is comprised of a hollow cup portion 49 which receives the screw, and two opposite transverse brackets. The cup 49 has a central longitudinal opening 40 having an inner diameter which slightly exceeds the diameter of the head 30 of the screw 21. This diameter is about 0.33 of an inch. The screw 21 passes through the opening 40 within the rod support 23 until the rear shoulder 34 of the screw 21 encounters a detaining flange 42 within the central opening 40 of the rod support 23. The flange 42 defines an opening 43 which has a diameter that exceeds the diameter of the shank 32. The diameter of the opening at the flange is about 0.27 of an inch. The detaining flange 42 has a sloped shoulder 44 which forms a socket for the rear shoulder 34 of the screw head 30. Thus, when the screw 21 engages the rod support, 23, a limited ball-and-socket joint is formed which permits freedom of movement between the rod support 23 and the screw 21.

The rod support 23 has two brackets 46, 47 which extend laterally from the cup portion 49 of the rod support 23. The brackets 46, 47 each have a groove 51, 52 on their upper surface of the proper diameter to cradle the rod 18. The grooves 51, 52 form a rod-receiving channel 54 which is about 0.69 of an inch long.

The bottom side of the brackets 46, 47 form buttressing curves 56, 57 where the brackets 46, 47 flow into the cup portion 49 of the rod support.

The cup 49 is reinforced in the area under the curve of the brackets 46, 47 so that the cup 49 includes two opposite reinforced portions 59, 60 having a larger external diameter (about 0.43 of an inch) which are separated by two curved walls 62, 63 having a smaller external diameter (about 0.35 of an inch).

The depth of the rod support 23 and the clamp 25 determines the amount that the anchor 16 projects beyond the lamina of the vertebrae. The rod support 23 has a total depth ranging from about 0.35 to about 0.52 of an inch including the brackets 46, 47 which extends about 0.11 of an inch above the cup 49. The rod-receiving channel 54 has a radius of about 0.13 of an inch and a depth of about 0.01 of an inch. The clamp 25 has a full height ranging from about 0.58 to about 0.74 of an inch, while the arch 72 has a height ranging from 0.51 to 0.67 of an inch.

On its bottom side, the cup 49 of the rod support 23 has an annular groove 65 so that the cup 49 includes annular teeth 66 which will bite into the bone as the rod support 23 is tightened into position.

The U-shaped clamp 25 includes a hollow central arch 72 defining two opposite, curved, externally-threaded walls 74, 75 having an outer diameter of about 0.50 of an inch. The arch is about 0.28 of an inch wide and has an inner radius at the top of about 0.14 of an inch. The walls 74, 75 are both grooved to form curved inner surfaces 78, 79. The inner surfaces 78, 79 of the walls 74, 75 are of the proper dimensions to engage the smaller diameter areas 62, 63 of the rod support 23, while the brackets 46, 47 and the reinforced portions 59, 60 of the rod support 23 fit within the arch 72 of the clamp 25. The reinforced areas 59, 60 of the rod support cup 49 complements the clamp 25 to form a hollow cylinder which captures the screw 21 along its longitudinal axis and which captures the rod 18 along its longitudinal axis transverse to the longitudinal axis of the screw.

The annular collar 27 includes internal threads 83 which engage the external threads 76 on the clamp 25. The collar 27 includes a plurality of holes 83 so that the collar can be tightened relative to the clamp 25. The clamp 25 likewise includes two holes 77 which permit the surgeon to use a holder to grasp the clamp 25. The collar 27 has holes 84 which permit the surgeon to use a crimping tool to partially strip the clamp threads 76 to prevent loosening of the clamp 25 but still allow removal of the collar 27 with a wrench.

As the collar 27 is rotated about the clamp 25, it cooperates with the underside of the brackets 46, 47 to tighten the clamp 25 in relation to the rod support 23. The rod 18 is grasped in the tunnel 84 formed between the rod-receiving channel 54 of the rod support 23 and the arch 72 of the clamp 25.

The anchor 16 was designed to deliver a high compressive force on the rod 18 when tightened with a special spanner wrench. This compressive force increases the limiting friction to decrease the possibility of rod slippage. This can be expressed by the formula below:

$$F_L = \mu_S R$$

where:

$F_L$ = limiting friction
$\mu_S$ = coefficient of static friction
$R$ = force applied to the surface.

This is an additional manner in which the current design is an improvement over prior art devices.

Figures 7, 8:
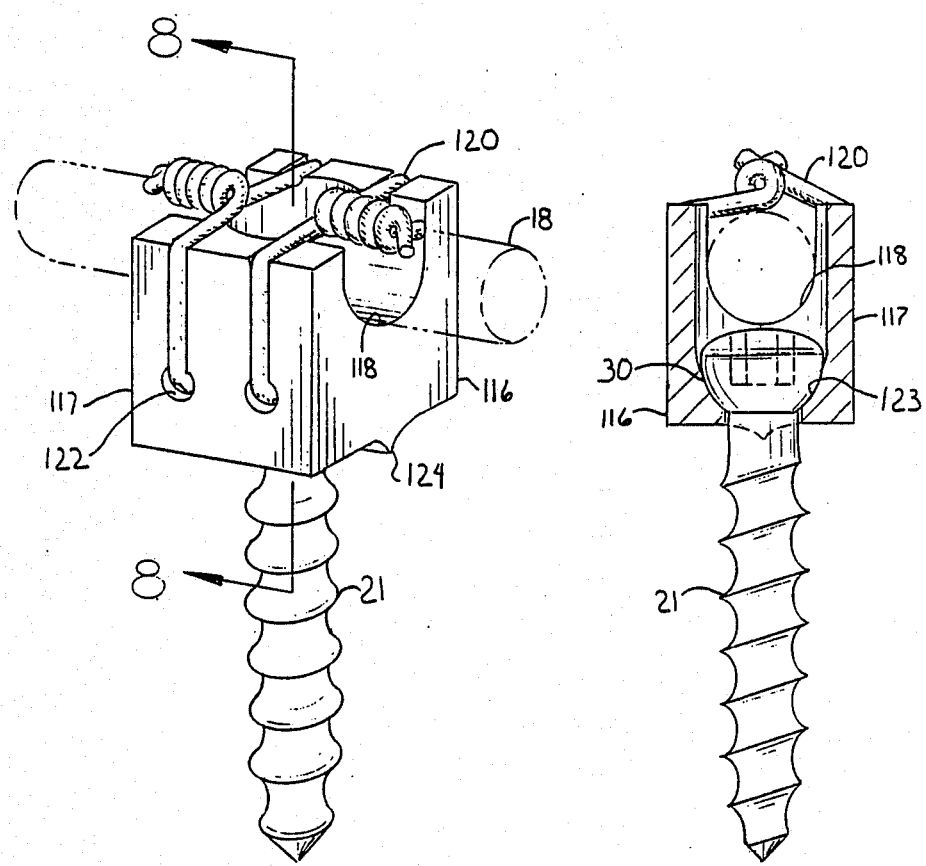
FIG. 7 is a perspective of the vertebral anchor and screw according to a second embodiment of the invention.
FIG. 8 is a cross-sectional view of the second embodiment of the invention, the plane of the section being indicated by line 8—8 in FIG. 7.

In the second embodiment of the present invention shown in FIG. 7, the rod support 116 includes a U-shaped head 117 which defines a rod-receiving channel 118 having a depth which exceeds the diameter of the rod 18. The rod 18 engages the channel 118 and is secured within the channel 118 by wires 120 which extend through bores 122 transverse to the longitudinal axis of the rod 18. The head 116 includes on its underside, two fillets 124 which act to grip the bone. In the second embodiment, the rod support 116 is countersunk 123 to accommodate the screw head 30.

In both embodiments, the screw may be an integral portion of the anchor. It is preferable however, that the screw is a separate member having the previously described freedom of movement. This allows for easier insertion without having to back out the screw in order to achieve proper alignment of the rod-receiving channels of the anchors. Further, this provides a bone-implant interface where micro-motion can occur upon fixation and dampen some of the load being transferred directly from the implant to the bone as well as decrease the degree of stress-shielding by the implant. This helps to compensate for the increased transfer of load to the bone-implant interface caused by the use of a more rigid implant which increases the likelihood of bony errosion by the screws.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way that is inconsistent with the extent to which the progress in the art has been advanced by the invention.

What is claimed is:

1. An anchor which secures a rod to a bone for the stabilization of the bone comprising:
    attachment means comprising a screw including a head and a threaded portion, the head having a larger outer diameter than the outer diameter of the threaded portion to define a rear shoulder;
    rod support means having a longitudinal axis and being attached to the bone about the longitudinal axis by the attachment means, the rod support means including a rod-receiving channel transverse to the longitudinal axis, the rod support means further including a cup having a rear opening and a hollow central recess, the cup also having a flange projecting into the rear opening, the hollow central recess receiving the head of the screw so that the threaded portion extends through the rear opening and the rear shoulder of the screw cooperates with the flange and is thereby adapted to hold the rod support means against a bone while allowing movement between the screw and the rod support means;
    a threaded clamp that engages the cup member of the rod support means and which cooperates with the rod support means to capture the rod independently of the engagement between said rear shoulder and said flange; and
an annular collar having threads which engage the threads of the clamp such that rotating the collar in relation to the cup exerts a compressive force on the rod to clamp the rod into position.

2. An apparatus for maintaining vertebrae in a desired relationship as set forth in claim 1 wherein said rod support includes means to secure the rod support from twisting axially out of alignment.

3. An internal fixation apparatus as set forth in claim 1 wherein:
said screw portion and said rod support are two members;
said screw portion having a threaded portion and a head, the rear portion of the head having a rounded shoulder;
the rod support including a cup portion having a central longitudinal opening, the rod support including at one end the channel and at the other end the central opening including a restricted diameter forming a lip which is smaller than the maximum diameter of the head such that when the screw is inserted through the central opening, the rounded shoulder engages the lip to form a ball-and-socket joint.

4. A device for the stabilization of one or more bone segments comprising two sets of implants, each implant set comprising:
a rod; and
at least two anchors, each anchor comprising a screw;
rod support means having a longitudinal axis and being adapted to be attached to a bone by a screw which extends into the bone along said longitudinal axis, so that the rod support means is held against the bone while allowing movement between the screw and the rod support means, the rod support means further including a rod-receiving channel transverse to the longitudinal axis;
a threaded clamp that engages the rod support means and which cooperates with the rod support means to capture the rod independently of the engagement between the screw and the rod support means; and
an annular collar having threads that engage the threads of the clamp such that rotating the collar in relation to the rod support means exerts a compressive force on the rod to clamp the rod into position.

5. A device for the stabilization of one or more bone segments as set forth in claim 4 wherein:
the screw includes a hear and a threaded portion, the head having a larger outer diameter than the outer diameter of the threaded portion to define a rear shoulder; and
the rod support means including a cup having a rear opening defining a flange projecting into the opening and a hollow central recess which receives the head of the screw so that the threaded portion extends through the rear opening and the rear shoulder of the screw cooperates with the flange to hold the rod support against the bone while allowing movement between the screw and the rod support.

6. An internal fixation apparatus for maintaining vertebrae in a desired relationship comprising:
a rod which is rigid and is biocompatible;
a plurality of vertebral anchors adapted to be positioned on the side of the spinous processes on the posterior surface of the transverse processes and the laminae and each anchor comprising
a screw,
a rod support which is adapted to be held to the vertebrae by the screw so that the rod support is held against a vertebrae while allowing movement between the screw and the rod support, the rod support having a channel which receives one of the rods,
a threaded clamp that engages the rod support and which cooperates with the rod support to capture the rod independently of the engagement between the screw and the rod support; and
an annular collar having threads that engage the threads of the clamp such that rotating the collar in relation to the rod support exerts a compressive force on the rod to clamp the rod into position.

7. A device for the posterior stabilization of the spine comprising two sets of spinal implants, each one adapted to be positioned on either side of the spinous process, each said of spinal implants comprising:
a rod; and
at least vertebral anchors, each anchor comprising
rod support means having a longitudinal axis and including
a cup having a rear opening defining a flange and a hollow central recess along the longitudinal axis, and
two opposite laterally-extending brackets which form a rod-receiving channel transverse to the longitudinal axis;
a transpedicular screw having a head defining a rear shoulder and a thread portion, the screw being engaged by the cup so that the rear shoulder cooperates with the flange and is thereby adapted to hold the rod support means against a bone while allowing movement between the screw and the rod support means;
an externally-threaded clamp having a central arch which cooperates with the rod support to enclose the rod between the central arch and the rod-receiving channel; and
an internally-threaded annular collar which cooperates with the externally-threaded portion of the clamp and the brackets to cause the clamp and the rod support to apply compressive force to the rod when the collar is tightened in relation to the clamp and is thereby adapted to hold the rod support means against a bone while allowing movement between the screw and the rod support means.

* * * * *

UNITED STATES PATENT AND TRADEMARK OFFICE
CERTIFICATE OF CORRECTION

PATENT NO. : 4,805,602

DATED : February 21, 1989

INVENTOR(S) : Rolando M. Puno and Kevin A. Kelly

It is certified that error appears in the above-identified patent and that said Letters Patent is hereby corrected as shown below:

Column 7, Line 54, "hear" should read --head--

Column 8, Line 31, "said" should read --set--

Signed and Sealed this

Fourteenth Day of November, 1989

*Attest:*

JEFFREY M. SAMUELS

*Attesting Officer*     *Acting Commissioner of Patents and Trademarks*